United States Patent [19]

Nakashima et al.

[11] Patent Number: 4,957,923
[45] Date of Patent: Sep. 18, 1990

[54] DIURETIC OR ANTIHYPERTENSIVE COMPOSITION

[75] Inventors: Mitsuyoshi Nakashima, Hamamatsu; Mitsutaka Kanamaru, Nagoya; Akira Sugiyama, Ikoma; Masato Terakawa, Nara; Takaharu Ono, Osaka; Haruo Horiai, Amagasaki, all of Japan

[73] Assignee: Fujisawa Pharmaceutical Co., Ltd., Osaka, Japan

[21] Appl. No.: 314,886

[22] Filed: Feb. 24, 1989

[30] Foreign Application Priority Data

Feb. 29, 1988 [JP] Japan .................... 63-48005
Feb. 29, 1988 [JP] Japan .................... 63-48006

[51] Int. Cl.$^5$ .......................... A61K 31/505
[52] U.S. Cl. ................................ 514/259
[58] Field of Search .......................... 514/259

[56] References Cited

U.S. PATENT DOCUMENTS 4,405,623 9/1983 Ishikawa et al. ............... 514/259
4,734,419 3/1988 Hashimoto et al. ............. 514/259

FOREIGN PATENT DOCUMENTS 0218999 4/1987 European Pat. Off. .
57-212178 12/1982 Japan .................... 514/259
62-96476 2/1987 Japan .

*Primary Examiner*—Allen J. Robinson
*Attorney, Agent, or Firm*—Oblon, Spivak, McClelland, Maier & Neustadt

[57] ABSTRACT

A method for treating edema or hypertension which comprises administering an effective amount of a quinazoline derivative of the general formula:

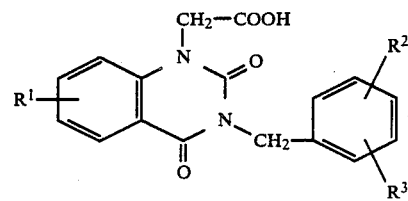

wherein $R^1$, $R^2$ and $R^3$ each is a hydrogen atom or a halogen atom or a pharmaceutically acceptable salt thereof to a human being in need of said treatment.

1 Claim, No Drawings

DIURETIC OR ANTIHYPERTENSIVE COMPOSITION

(INDUSTRIAL FIELD OF UTILIZATION)

This invention relates to a diuretic or antihypertensive composition comprising a quinazoline derivative of the following general formula (I) or a pharmaceutically acceptable salt thereof as an active ingredient, and, as such, finds application in the field of health care.

(PRIOR ART)

The quinazoline derivative (I) according to this invention is a known compound and has been demonstrated to have aldose reductase-inhibitory activity [Japanese Unexamined Patent Application KOKAI 62-96476 (1987)]. It is not known, however, that the derivative has diuretic or antihypertensive activity.

(CONSTRUCTION OF THE INVENTION)

This invention relates to a diuretic or antihypertensive composition comprising a quinazoline derivative of the general formula (I):

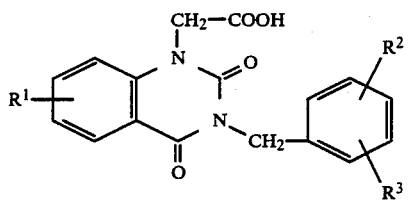

wherein $R^1$, $R^2$ and $R^3$ each is a hydrogen atom or a halogen atom or a pharmaceutically acceptable salt thereof as an active ingredient.

In the above definition of quinazoline derivative (I), the halogen designated independently by $R^1$, $R^2$ and $R^3$ includes chlorine, bromine, iodine and fluorine.

The pharmaceutically acceptable salt of quinazoline derivative (I) includes salts with inorganic bases such as alkali metals (e.g. sodium, potassium, etc.) and alkaline earth metals (e.g. calcium, magnesium, etc.), ammonium salts, salts with organic bases such as organic amines (e.g. triethylamine, pyridine, picoline, ethanolamine, triethanolamine, dicyclohexylamine, N,N'-dibenzylethylenediamine, etc.), salts with basic amino acids (e.g. arginine etc.) and the like.

The quinazoline derivative (I) and pharmaceutically acceptable salts according to this invention have diuretic and antihypertensive activities and are, therefore, of value as the active ingredient of diuretic or antihypertensive composition.

The diuretic composition according to this invention is effective in the treatment and prevention of edema or the like, and the antihypertensive composition is effective in the treatment and prevention of hypertension or the like. The active ingredient, quinazoline derivative (I) or pharmaceutically acceptable salt thereof, may be administered as such but is generally administered as formulated into various pharmaceutically acceptable compositions.

As dosage forms useful for such compositions, there may be mentioned injections, capsules, granules, powders, tablets and so on.

Such pharmaceutical compositions are formulated by the established pharmaceutical procedures using excipients (e.g. sucrose, starch, mannit, sorbit, lactose, glucose, cellulose, talc, calcium phosphate, calcium carbonate, etc.), binding agents (e.g. cellulose, methyl cellulose, hydroxypropylmethyl cellulose, polypropylpyrrolidone, gelatin, gum arabic, polyethylene glycol, sucrose, starch, etc.), disintegrators (e.g. starch, carboxymethyl cellulose, hydroxypropyl starch, sodium bicarbonate, calcium phosphate, calcium citrate, etc.), lubricants (e.g. magnesium stearate, talc, sodium laurylsulfate, etc.), flavoring agents (e.g. citric acid, mentol, glycine, orange powders, etc.), preservatives (e.g. sodium benzoate, sodium bisulfite, methylparaben, propylparaben, etc.), stabilizers (e.g. citric acid, sodium citrate, acetic acid, etc.), suspending agents (e.g. methyl cellulose, polyvinylpyrrolidone, aluminum stearate, etc.), dispersing agents (e.g. hydroxypropylmethyl cellulose, etc.), solvents (e.g. water, etc.), base wax (e.g. cacao butter, white petrolatum, polyethylene glycol, etc.) and so on.

While the dosage of the diuretic or antihypertensive composition according to this invention is dependent on the patient's age and body weight, clinical condition, method of administration, etc., a daily dose of generally 10 to 1800 mg as quinazoline derivative (I) or a pharmaceutically acceptable salt thereof, or preferably 30 to 1200 mg on the same basis, is administered orally or parenterally in a single dose to 3 divided doses.

The following test examples are intended to illustrate the excellent diuretic action, antihypertensive action and low toxicity of the quinazoline derivative (I) or pharmaceutically acceptable salt thereof.

Test compound (1) 2-[7-Chloro-3-(4-bromo-2-fluorobenzyl)-1,2,3,4-tetrahydro-2,4-dioxoquinazolin-1-yl]acetic acid (hereinafter referred to briefly as compound A).

(2) 2-[7-Fluoro-3-(4-bromo-2-fluorobenzyl)-1,2,3,4-tetrahydro-2,4-dioxoquinazolin-1-yl]acetic acid (hereinafter referred to briefly as compound B). ( (a) Diuretic action (human):

Method:

To healthy male adult volunteers, 300 mg (the capsule of Example 3 below ×1) (6 men) or 600 mg (the capsule of Example 3 below ×2) (6 men) of compound A was orally 20 administered in fasting condition, or 600 mg (the capsule of Example 3 below×2) (6 men) of compound A was orally administered 30 minutes after breakfast. In each group, the 24-hr urine volume before administration and that on day 1 after administration were respectively determined.

The results are shown in the following table 1.

TABLE 1

| Dosage of Compound A (mg) | Urine volume (ml), mean ± S.D. Urine sampling intervals (hr) | | | | | |
|---|---|---|---|---|---|---|
| | −24–0 | 0–2 | 2–4 | 4–8 | 8–12 | 12–24 |
| 300 (without breakfast) | 902 ± 256 | 95 ± 57 | 136 ± 60 | 328 ± 55 1508 ± 274 | 340 ± 79 | 609 ± 147 |
| 600 (without breakfast) | 982 ± 293 | 64 ± 24 | 82 ± 32 | 292 ± 50 1693 ± 368 | 393 ± 141 | 863 ± 253 |

TABLE 1-continued

| Dosage of Compound A (mg) | Urine volume (ml), mean ± S.D. Urine sampling intervals (hr) | | | | | |
|---|---|---|---|---|---|---|
| | −24−0 | 0−2 | 2−4 | 4−8 | 8−12 | 12−24 |
| 600 (30 min after breakfast) | 1234 ± 212 | 130 ± 46 | 151 ± 19 | 414 ± 161 2031 ± 362 | 507 ± 139 | 829 ± 240 |

Diuretic action (rats)

Method:

Female SD rats aged 6 weeks (9 rats per dosage) were used. After an 18-hour fast, the rats were dosed with the test drug and, at the same time, orally loaded with 20 ml/kg of physiological saline. The rats were then placed in metabolism cages, 3 animals per cage, and the 0–6 hour and 6–24 hour urines were collected. Meanwhile, the animals were additionally loaded with 25 ml/kg of physiological saline immediately after collection of the 0–6 hour urine. Na+ in urine was determined with STAT/ION II (Technicon).

The results were respectively converted to the amounts of excretion per kg rat body weight, which were then tabulated as the mean±S.E. for each dose level.

The drug was suspended in 0.5% methylcellulose at necessary concentrations and 5 ml/kg of each suspension was orally administered. The control group similarly received 0.5% methylcellulose only.

The results are set forth below in Table 2.

TABLE 2

| Dosage of Compound B (mg/kg) | Number of cases (3 animals per case) | Urine volume (ml/kg) Urine sampling intervals (hr) | | Na+(μEq/kg) Urine sampling intervals (hr) | |
|---|---|---|---|---|---|
| | | 0−6 | 6−24 | 0−6 | 6−24 |
| 0 (Control) | 3 | 13.2 ± 2.0 | 26.59 ± 2.24 39.78 ± 4.26 | 1460 ± 173 | 3830 ± 463 5289 ± 636 |
| 100 | 3 | 30.1 ± 1.5** | 33.69 ± 0.55* 63.75 ± 1.19** | 2416 ± 101** | 3940 ± 295 6356 ± 311 |
| 320 | 3 | 37.9 ± 1.5** | 61.22 ± 6.20** 99.10 ± 6.64** | 3021 ± 440* | 5861 ± 194* 8882 ± 630* |

*, **: Significantly different from control at 5% and 1% levels, respectively.

(c) Diuretic action (beagle dogs)

Method:

Female beagle dogs weighing 8 to 10 kg were used (6 dogs per group). After an 18-hour fast, the animals were orally dosed with 5 ml/kg of suspensions of the drug in 0.5% methylcellulose and, at the same time, orally loaded with 15 ml/kg of physiological saline and the 0–6 hr and 6–24 hr urines were collected. Meanwhile, the dogs were additionally loaded with 20 ml/kg of physiological saline immediately after collection of the 0–6 hr urine. Na+ in urine was determined with STAT-/ION (Technicone).

The results were respectively converted to the amounts of excretion per kg body weight, which were then tabulated as the mean±S.E. for each dose level. The control group similarly received 0.5% methylcellulose instead of the drug.

The results are set forth below in Table 3.

TABLE 3

| Dosage of compound B (mg/kg) | Number of cases | Urine volume (ml/kg) | NA+ (μEq/kg) |
|---|---|---|---|
| 0 (Control) | 6 | 5.8 ± 1.4 | 544 ± 133 |
| 100 | 6 | 13.3 ± 2.6* | 1068 ± 280 |

*Significantly different from control at 5% level.

(d) Antihypertension action (DOCA hypertensive rats):

Method:

Male Wistar rats, 10 weeks old, were subjected to left nephrectomy and 2 to 4 days after operation, deoxycorticosterone acetate was administered subcutaneously in a dose of 30 mg/ml/kg twice a week. The animals were given 1% saline for drinking water and the individuals showing a mean blood pressure of ≧150 mmHg at 15 weeks of age were submitted to the experiment. After catheterization, saline for drinking water was replaced with tap water. At the beginning of the experiment, the test rats had mean blood pressures from 152 to 204 mmHg, heart rates from 354 to 462 beats/min. and body weights from 232 to 318 g. 3∼5 Animals per group were used.

3 Or 4 days before the beginning of the experiment, one end of a catheter for blood pressure measurement was passed from the femoral artery to the abdominal aorta of each rat and the other end was passed beneath the skin and fixed in exposed position in the dorsocervical region. The drug was orally administered once a day for 5 consecutive days. The rats had been deprived of food for about 3 hours before drug administration. The blood pressure was measured before administration and 5 hours after administration of days 1, 3 and 5. At each blood pressure measurement, the mean blood pressure was observed via a pressure transducer connected to the dorsocervical end of the catheter for blood pressure measurement and the stabilized mean blood pressure was recorded.

Drug was suspended and diluted using a 0.5% solution of methylcellulose and 5ml/kg of the suspension was orally administered.

The results are shown in Tables 4 and 5.

TABLE 4

| Dosage of compound A (mg/kg) | Number of cases | | Day 1 before administration | Day 1 After 5 hr | Day 3 Before administration | Day 3 After 5 hr | Day 5 Before administration | Day 5 After 5 hr |
|---|---|---|---|---|---|---|---|---|
| 0 (Control) | 5 | Mean Blood pressure (mm Hg) | 165 ±5 | 161 ±4 | 156 ±3 | 153 ±2 | 164 ±7 | 149 ±7 |
| | | Percentage of change | 0.0 ±0.0 | −1.9 ±3.2 | −5.2 ±3.9 | −7.2 ±2.6 | −0.3 ±3.9 | −9.3 ±4.3 |
| 3.2 | 4 | Mean blood pressure (mm Hg) | 175 ±11 | 148 ±11 | 153 ±14 | 142 ±7 | 139 ±15 | 131 ±11 |
| | | Percentage of change | 0.0 ±0.0 | −15.6* ±2.7 | −13.4 ±2.9 | −18.6* ±3.3 | −21.0* ±4.4 | −24.9 ±6.7 |
| 10 | 4 | Mean blood pressure (mm Hg) | 166 ±5 | 145 ±9 | 137 ±8 | 127 ±6 | 127 ±4 | 118 ±7 |
| | | Percentage of change | 0.0 ±0.0 | −13.0 ±4.3 | −17.2 ±5.7 | −23.1* ±4.8 | −23.2** ±3.9 | −29.1** ±3.0 |
| 32 | 3 | Mean blood pressure (mm Hg) | 168 ±16 | 133 ±7 | 133 ±4 | 132 ±2 | 117 ±5 | 116 ±6 |
| | | Percentage of change | 0.0 ±0.0 | −20.1 ±3.1 | −19.2 ±7.7 | −20.1 ±7.1 | −29.5 ±3.2 | −30.2* ±4.9 | mean ± S.E.
*, **: Significantly different from control at 5% and 1% levels, respectively.

TABLE 5

| Dosage of compound B (mg/kg) | Number of cases | | Day 1 before administration | Day 1 After 5 hr | Day 3 Before administration | Day 3 After 5 hr | Day 5 Before administration | Day 5 After 5 hr |
|---|---|---|---|---|---|---|---|---|
| 0 (Control) | 5 | Mean blood pressure (mm Hg) | 165 ±5 | 161 ±4 | 156 ±3 | 153 ±2 | 164 ±7 | 149 ±7 |
| | | Percentage of change | 0.0 ±0.0 | −1.9 ±3.2 | −5.2 ±3.9 | −7.2 ±2.6 | −0.3 ±3.9 | −9.3 ±4.3 |
| 3.2 | 4 | Mean blood pressure (mm Hg) | 193 ±5 | 176 ±7 | 175 ±5 | 160 ±4 | 167 ±5 | 161 ±7 |
| | | Percentage of change | 0.0 ±0.0 | −8.9 ±1.4 | −9.3 ±1.7 | −17.1* ±1.2 | −13.5* ±1.6 | −16.7 ±2.3 |
| 10 | 3 | Mean blood pressure (mm Hg) | 180 ±14 | 148 ±8 | 137 ±4 | 132 ±4 | 139 ±7 | 143 ±8 |
| | | Percentage of change | 0.0 ±0.0 | −17.5* ±2.0 | −23.3* ±5.1 | −26.1** ±3.8 | −22.5* ±4.0 | −20.0 ±3.1 |
| 100 | 4 | Mean blood pressure (mm Hg) | 176 ±5 | 151 ±13 | 144 ±12 | 130 ±6 | 138 ±15 | 135 ±12 |
| | | Percentage of change | 0.0 ±0.0 | −14.5 ±5.0 | −18.4 ±4.9 | −26.2** ±1.8 | −22.3* ±6.2 | −23.6 ±5.1 | mean ± S.E.
*, **: Significantly different from control at 5% and 1% levels, respectively.

(e) Antihypertensive action (human)

Method:

To 6 healthy male adult volunteers, 150 mg of compound A (one capsule each of capsules shown in Examples 1 and 2 below) was orally administered twice a day at a 12-hour interval from 30 minutes after breakfast to 2 hours after supper for 8 consecutive days (except on day 8 when the administration was made only once in the morning) and the systolic blood pressure in standing position was measured.

The results are shown in Table 6.

TABLE 6

| | Systolic blood pressure in standing position (mean ± S.D., mmHg): measured immediately before breakfast | | | | | | | | | |
|---|---|---|---|---|---|---|---|---|---|---|
| | Day 1 | Day 2 | Day 3 | Day 4 | Day 5 | Day 6 | Day 7 | Day 8 | Day 9 | Day 10 |
| | 121 ± 8 | 113 ± 6 | 114 ± 7 | 114 ± 5 | 110 ± 8 | 114 ± 6 | 116 ± 8 | 117 ± 5 | 113 ± 3 | 117 ± 6 |

(f) Acute toxicity:

Male SD rats (5 animals per group) were orally dosed with a suspension of the test compound in 0.5% methylcellulose solution and observes in 14 days after oral administration.

| Results | |
|---|---|
| | LD$_{50}$ |
| Compound A | 4250 mg/kg |
| Compound B | 2144 mg/kg |

(EXAMPLES)

Example 1

A powder of the following formula is encapsulated to provide a capsule.

| Formula | |
|---|---|
| Compound A | 100 mg |
| Low-substituted hydroxypropylcellulose | 10 mg |
| Polyoxyl 40 Stearate | 1 mg |
| Hydroxypropylcellulose | 1 mg |

Example 2

A powder of the following formula is encapsulated to provide a capsule.

| Formula | |
|---|---|
| Compound A | 50 mg |
| Low-substituted hydroxypropylcellulose | 5 mg |
| Polyoxyl 40 Stearate | 0.5 mg |
| Hydroxypropylcellulose | 0.5 mg |

Example 3

A powder of the following formula is encapsulated to provide a capsule.

| Formula | |
|---|---|
| Compound A | 300 mg |
| Low-substituted hydroxypropylcellulose | 30 mg |
| Polyoxyl 40 Stearate | 3 mg |
| Hydroxypropylcellulose | 3 mg |

Example 4

The ingredients in the following formula are blended and granulated into granules in a conventional manner.

| Formula for granules | |
|---|---|
| Compound A | 30.0% (by weight) |
| Lactose | 69.4% |
| Polyoxyl 40 Stearate | 0.1% |
| Hydroxypropylcellulose | 0.5% |

Example 5

The ingredients in the following formula are blended and powdered into powders in a conventional manner.

| Formula for powders | |
|---|---|
| Compound A | 30.0% (by weight) |
| Lactose | 69.4% |
| Polyoxyl 40 Stearate | 0.1% |
| Hydroxypropylcellulose | 0.5% |

Example 6

The ingredients in the following formula are blended and compressed into tablets in a conventional manner.

| Formula for a tablet | |
|---|---|
| Compound A | 300 (mg) |
| Lactose | 100.8 |
| Cross-Linked sodium carboxymethylcellulose | 9 |
| Hydroxypropylcellulose | 3 |
| Polyoxyl 40 Stearate | 3 |
| Magnesium Stearate | 4.2 |
| | 420 mg/tablet |

Thus obtained tablets are, when desired, coated with film-coating or enteric coating.

Example 7

Compound A (5 g) and sodium hydroxide (450 mg) are dissolved in distilled water for injection to give injectable solution (10 l) and the injectable solution is divided to 100 ampoules in a conventional manner.

Example 8

The above-mentioned compositions (capsule, granule, powder, tablet, injection) are also prepared by using compound B instead of compound A.

What we claim is:

1. A method for treating edema or hypertension which comprises administering an effective amount of a quinazoline derivative of the formula:

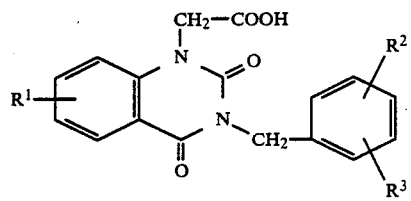

wherein $R^1$, $R^2$ and $R^3$ each is a hydrogen atom or a halogen atom or a pharmaceutically acceptable salt thereof to a human being in need of said treatment.

* * * * *